(12) United States Patent
Lee et al.

(10) Patent No.: US 12,419,982 B2
(45) Date of Patent: Sep. 23, 2025

(54) ROBOT

(71) Applicant: LG ELECTRONICS INC., Seoul (KR)

(72) Inventors: Haklim Lee, Seoul (KR); Jiyong Shin, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 406 days.

(21) Appl. No.: 18/021,681

(22) PCT Filed: Aug. 24, 2020

(86) PCT No.: PCT/KR2020/011271
§ 371 (c)(1),
(2) Date: Feb. 16, 2023

(87) PCT Pub. No.: WO2022/045381
PCT Pub. Date: Mar. 3, 2022

(65) Prior Publication Data
US 2023/0310683 A1    Oct. 5, 2023

(51) Int. Cl.
*A61L 2/24* (2006.01)
*A61L 2/10* (2006.01)
(Continued)

(52) U.S. Cl.
CPC ..................... *A61L 2/24* (2013.01);
*A61L 2/10* (2013.01); *B25J 5/007* (2013.01);
*B25J 11/0085* (2013.01);
(Continued)

(58) Field of Classification Search
CPC .......... A61L 2/24; A61L 2/10; A61L 2202/11; A61L 2202/14; A61L 2202/16; B25J 5/007; B25J 11/0085; B25J 9/16; B25J 15/02
See application file for complete search history.

(56) References Cited

U.S. PATENT DOCUMENTS 9,023,274 B2 * 5/2015 Garner ................ A61L 2/24
422/186.05
2006/0284109 A1    12/2006 Scheir et al.
(Continued)

FOREIGN PATENT DOCUMENTS

KR    10-2011-0140048    12/2011
KR    10-2014-0051219     4/2014
(Continued)

OTHER PUBLICATIONS

PCT International Application No. PCT/KR2020/011271, International Search Report dated Apr. 23, 2021, 6 pages.

*Primary Examiner* — Tony Ko
(74) *Attorney, Agent, or Firm* — Birch, Stewart, Kolasch & Birch, LLP

(57) ABSTRACT

A robot according to an embodiment of the present invention can comprise: a pair of recessed parts formed on both surfaces of a main body, vertically extended, and opened with respect to the upper side thereof; a flexible plate including a pair of vertical parts vertically sliding along the pair of recessed parts, and a connecting part connecting the pair of vertical parts to each other and being convexly bent downward; a chain coupled to both edges of the flexible plate and extended in the longitudinal direction of the flexible plate; a plurality of ultraviolet lamps connected to the flexible plate or the chain and spaced from each other in parallel; and a rotator which includes a gear part gear-coupled to the chain and which is disposed in the inner space of the main body.

19 Claims, 14 Drawing Sheets

(51) Int. Cl.
  *B25J 5/00* (2006.01)
  *B25J 11/00* (2006.01)
(52) U.S. Cl.
  CPC ........ *A61L 2202/11* (2013.01); *A61L 2202/14* (2013.01); *A61L 2202/16* (2013.01)

(56) References Cited

U.S. PATENT DOCUMENTS

2012/0313014 A1 12/2012 Stibich et al.
2021/0353808 A1* 11/2021 Hung .................. G05D 1/0242

FOREIGN PATENT DOCUMENTS

KR 10-1635593 7/2016
KR 10-1724447 4/2017

\* cited by examiner

ROBOT

CROSS-REFERENCE TO RELATED APPLICATION

This application is the National Stage filing under 35 U.S.C. 371 of International Application No. PCT/KR2020/011271, filed on Aug. 24, 2020, the contents of which are hereby incorporated by reference herein its entirety.

TECHNICAL FIELD

The present invention relates to a robot capable of self-driving.

BACKGROUND ART

To take on a part of factory automation, robots have been developed for industrial use. In recent years, the field of application of robots has been further expanded, and not only medical robots and aerospace robots, but also robots that can be used in daily life are being developed.

These robots for everyday life provide specific services (example, shopping, serving, talking, cleaning, etc.) in response to a user's command.

However, existing robots for everyday life are designed to provide only specific services, and thus there is a problem in that utilization is not high compared to the cost invested in developing the robot.

Accordingly, the need for a robot capable of providing various services has recently emerged.

In particular, robots are suitable for carrying out tasks such as sterilization, quarantine, and disinfection, which are difficult or dangerous tasks for humans to perform. In general, a sterilization robot employs an ultraviolet sterilization method.

However, the conventional ultraviolet sterilization robot has a problem in that it is difficult to irradiate ultraviolet rays close to a high position, such as an upper wall, or the size is too large to irradiate ultraviolet rays up to a high position.

DISCLOSURE

Technical Problem

The problem to be solved by the present invention is to provide a robot capable of performing ultraviolet sterilization to a high position while maintaining a compact size.

Technical Solution

A robot according to an embodiment of the present disclosure may comprise: a main body disposed above the base and having an inner space; a pair of depression portions formed on both sides of the main body, extending vertically, and open to an upper side; a pair of through holes formed through a lower part of the pair of depression portions and connected with the inner space of the main body; a flexible plate including a pair of vertical portions vertically sliding along the pair of depression portions and a connecting portion connecting the pair of vertical portions to each other through the through hole and convexly bent downward; a chain coupled to the flexible plate and extending along a longitudinal direction of the flexible plate; a plurality of ultraviolet lamps connected to the flexible plate or chain and spaced apart from each other; and a rotator including a gear unit coupled with the chain and disposed in the inner space of the main body.

If the rotator rotates, one of the pair of vertical portions may rise to a height protruding upward from the main body.

Wherein guide grooves extending vertically and guiding vertical sliding of the chain may be formed on both inner surfaces of the depression portion.

Wherein a plurality of ribs may be protruded from an outer surface of the flexible plate, and are spaced parallel to each other, with the plurality of ultraviolet lamps interposed therebetween.

The robot may further comprise a plurality of reflectors disposed between the plurality of ribs passing between the plurality of ultraviolet lamps and the flexible plate.

Wherein the reflector may be bent to surround the outer circumference of the ultraviolet lamp at a distance.

The robot may further comprise a support sheet having a pair of support portions for supporting the vertical portion from the inside, and a bending portion connecting the pair of support portions and corresponding to the connection portion.

Wherein the pair of support portions may be convexly curved toward the inner surface of the flexible plate with respect to a vertical axis.

Wherein the rotator may be located on the upper side of the connection portion, and the bending portion may be located between the outer circumference of the rotator and the inner surface of the connection portion.

The robot may further comprise a guide hole formed through the support sheet and extending in the longitudinal direction of the support sheet; and a guide pin protruding from the flexible plate and inserted into the guide hole.

Wherein a stopper may be equipped with the chain for preventing the chain from bending outward.

The robot may further comprise a weight body connected to the rotator and whose position is variable according to the rotation of the rotator, wherein the weight body may be moved to approach a vertical portion having a lowered height among the pair of vertical portions or is eccentric toward the one vertical portion.

The robot may further comprise a lower ultraviolet lamp disposed on the lower side of the base.

The robot further comprises a lower reflector passing between a lower surface of the base and an outer circumference of the lower ultraviolet lamp.

Wherein the base may comprise: a base plate on which the lower ultraviolet lamp is installed; and a case surrounding the circumference of the base plate, wherein a height between the bottom surface contacted by the driving wheel and the lower ultraviolet lamp is greater than a height between the bottom surface and the lower end of the case.

Wherein the plurality of ultraviolet lamps may comprise: a first ultraviolet lamp corresponding to the vertical portion and positioned inside the depression portion or above the depression portion; and a second ultraviolet lamp corresponding to the connecting portion and located in the inner space of the main body.

The robot may further comprise a light guide path disposed inside the base for guiding the ultraviolet rays emitted from the second ultraviolet lamp to a bottom surface in contact with the driving wheel.

The robot may further comprise a mirror provided on an inner circumference of the light guide passage; or at least one of convex lenses disposed inside the light guide passage.

The robot may further comprise further comprises: a sensor for detecting a height of at least one of the pair of vertical portions; and a processor for limiting the rotational speed of the driving wheel if the detected value of the sensor is out of a predetermined range.

Advantageous Effects

According to a preferred embodiment of the present invention, the height of the sterilization module can be adjusted. As a result, the robot can approach the sterilization target (for example, a wall) with the height of the sterilization module elevated, and can perform powerful ultraviolet sterilization up to a high position.

In addition, the sterilization module may slide along the depression portion formed on both sides of the main body. In this way, the height of the sterilization module can be easily adjusted, and it is possible to bring the sterilization module close enough to the sterilization target.

In addition, the sterilization module may rise to a height protruding upward from the main body. Therefore, it is possible to perform ultraviolet sterilization up to a place higher than the height of the main body while maintaining a compact size of the robot.

In addition, since the sterilization module faces both sides of the main body, one side of the direction where the sterilization target is located among both sides of the sterilization module may be raised. As a result, the driving line of the robot for sterilizing the sterilization target can be simplified.

In addition, the sterilization efficiency of the ultraviolet sterilization module may be further improved by the reflector provided in the sterilization module.

In addition, by the guide grooves formed on both inner surfaces of the depression portion, bending of the vertical portion of the flexible plate can be prevented and vertical sliding can be guided.

In addition, by the support sheet as a bi-stable member, even if the vertical portion of the flexible plate protrudes upward from the main body, it can be supported without bending inward.

In addition, by the stopper provided on the chain, even if the vertical portion of the flexible plate protrudes upward from the main body, it can be supported without being bent outward.

In addition, by the weight body whose position is variable according to the rotation of the rotator, it is possible to offset the weight bias caused by the elevation of one side of the sterilization module. As a result, the robot can run stably even if the sterilization module is elevated.

In addition, the bottom surface on which the robot travels can be sterilized by ultraviolet rays using a lower ultraviolet lamp or a light guide passage.

In addition, the height of the lower Ultraviolet lamp may be higher than the height of the lower end of the case included in the base based on the bottom surface. As a result, it is possible to prevent leakage of ultraviolet rays emitted from the lower Ultraviolet lamp to the surroundings and to improve sterilization efficiency of the floor surface.

In addition, the sliding state of the sterilization module can be detected by the sensor, and the robot can be controlled to travel slowly in a state where one side of the sterilization module is elevated. Thus, stable driving of the robot according to the sliding state of the sterilization module is possible.

BEST MODE

Figure 1:
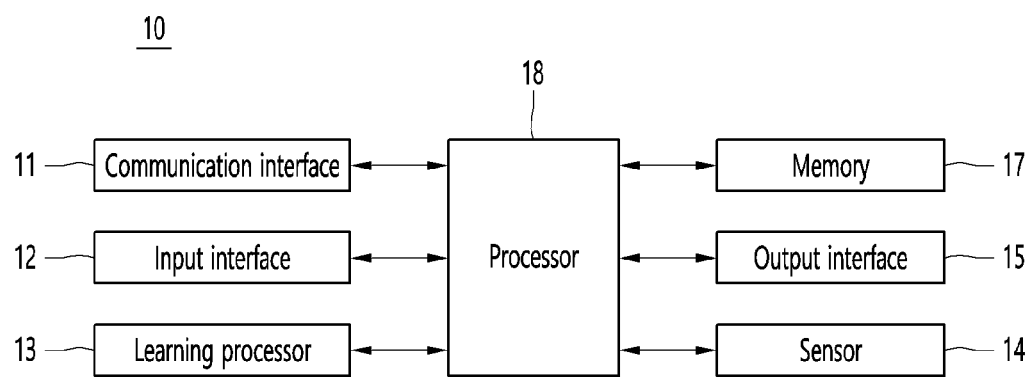
FIG. 1 shows an AI device including a robot according to an embodiment of the present invention.

Hereinafter, detailed embodiments will be described in detail with reference to the accompanying drawings.

Hereinafter, an expression "an element is "coupled" or "connected" to another element" may means that the two elements are directly coupled or connected to each other, or may mean that a third element is present between the two elements and the two elements are coupled or connected to each other by the third element. On the other hand, if it is described that one element is "directly coupled" or "directly connected" to another element, it may be understood that a third element is not present between the two elements.

<Robot>

A robot may refer to a machine that automatically processes or operates a given task by its own ability. In particular, a robot having a function of recognizing an environment and performing a self-determination operation may be referred to as an intelligent robot.

Robots may be classified into industrial robots, medical robots, home robots, military robots, and the like according to the use purpose or field.

The robot includes a driving unit may include an actuator or a motor and may perform various physical operations such as moving a robot joint. In addition, a movable robot may include a wheel, a brake, a propeller, and the like in a driving unit, and may travel on the ground through the driving unit or fly in the air.

<Artificial Intelligence (AI)>

Artificial intelligence refers to the field of studying artificial intelligence or methodology for making artificial intelligence, and machine learning refers to the field of defining various issues dealt with in the field of artificial intelligence and studying methodology for solving the various issues. Machine learning is defined as an algorithm that enhances the performance of a certain task through a steady experience with the certain task.

An artificial neural network (ANN) is a model used in machine learning and may mean a whole model of problem-solving ability which is composed of artificial neurons (nodes) that form a network by synaptic connections. The artificial neural network can be defined by a connection pattern between neurons in different layers, a learning process for updating model parameters, and an activation function for generating an output value.

The artificial neural network may include an input layer, an output layer, and optionally one or more hidden layers. Each layer includes one or more neurons, and the artificial neural network may include a synapse that links neurons to neurons. In the artificial neural network, each neuron may output the function value of the activation function for input signals, weights, and deflections input through the synapse.

Model parameters refer to parameters determined through learning and include a weight value of synaptic connection and deflection of neurons. A hyperparameter means a parameter to be set in the machine learning algorithm before learning, and includes a learning rate, a repetition number, a mini batch size, and an initialization function.

The purpose of the learning of the artificial neural network may be to determine the model parameters that minimize a loss function. The loss function may be used as an index to determine optimal model parameters in the learning process of the artificial neural network.

Machine learning may be classified into supervised learning, unsupervised learning, and reinforcement learning according to a learning method.

The supervised learning may refer to a method of learning an artificial neural network in a state in which a label for learning data is given, and the label may mean the correct answer (or result value) that the artificial neural network must infer if the learning data is input to the artificial neural network. The unsupervised learning may refer to a method of learning an artificial neural network in a state in which a label for learning data is not given. The reinforcement learning may refer to a learning method in which an agent defined in a certain environment learns to select a behavior or a behavior sequence that maximizes cumulative compensation in each state.

Machine learning, which is implemented as a deep neural network (DNN) including a plurality of hidden layers among artificial neural networks, is also referred to as deep learning, and the deep learning is part of machine learning. In the following, machine learning is used to mean deep learning.
<Self-Driving>

Self-driving refers to a technique of driving for oneself, and a self-driving vehicle refers to a vehicle that travels without an operation of a user or with a minimum operation of a user.

For example, the self-driving may include a technology for maintaining a lane while driving, a technology for automatically adjusting a speed, such as adaptive cruise control, a technique for automatically traveling along a predetermined route, and a technology for automatically setting and traveling a route if a destination is set.

The vehicle may include a vehicle having only an internal combustion engine, a hybrid vehicle having an internal combustion engine and an electric motor together, and an electric vehicle having only an electric motor, and may include not only an automobile but also a train, a motorcycle, and the like.

At this time, the self-driving vehicle may be regarded as a robot having a self-driving function.

FIG. 1 shows an AI device including a robot according to an embodiment of the present invention.

The AI device 10 may be implemented by a stationary device or a mobile device, such as a TV, a projector, a mobile phone, a smartphone, a desktop computer, a notebook, a digital broadcasting terminal, a personal digital assistant (PDA), a portable multimedia player (PMP), a navigation device, a tablet PC, a wearable device, a set-top box (STB), a DMB receiver, a radio, a washing machine, a refrigerator, a desktop computer, a digital signage, a robot, a vehicle, and the like.

Referring to FIG. 1, the AI device 10 may include a communication interface 11, an input interface 12, a learning processor 13, a sensor 14, an output interface 15, a memory 17, and a processor 18.

The Communication interface 11 may transmit and receive data to and from external devices such as other AI devices 10a to 10e and the AI server 20 by using wire/wireless communication technology. For example, the Communication interface 11 may transmit and receive sensor information, a user input, a learning model, and a control signal to and from external devices.

The communication technology used by the communication interface 11 includes GSM (Global System for Mobile communication), CDMA (Code Division Multi Access), LTE (Long Term Evolution), 5G, WLAN (Wireless LAN), Wi-Fi (Wireless-Fidelity), Bluetooth™, RFID (Radio Frequency Identification), Infrared Data Association (IrDA), ZigBee, NFC (Near Field Communication), and the like.

The input interface 12 may acquire various kinds of data.

At this time, the input interface 12 may include a camera for inputting a video signal, a microphone for receiving an audio signal, and a user input interface for receiving information from a user. The camera or the microphone may be treated as a sensor, and the signal acquired from the camera or the microphone may be referred to as sensing data or sensor information.

The input interface 12 may acquire a learning data for model learning and an input data to be used if an output is acquired by using learning model. The input interface 12 may acquire raw input data. In this case, the processor 18 or the learning processor 13 may extract an input feature by preprocessing the input data.

The learning processor 13 may learn a model composed of an artificial neural network by using learning data. The learned artificial neural network may be referred to as a learning model. The learning model may be used to an infer result value for new input data rather than learning data, and the inferred value may be used as a basis for determination to perform a certain operation.

At this time, the learning processor 13 may perform AI processing together with the learning processor 24 of the AI server 20.

At this time, the learning processor 13 may include a memory integrated or implemented in the AI device 10. Alternatively, the learning processor 13 may be implemented by using the memory 17, an external memory directly connected to the AI device 10, or a memory held in an external device.

The sensor 14 may acquire at least one of internal information about the AI device 10, ambient environment information about the AI device 10, and user information by using various sensors.

Examples of the sensors included in the sensor 14 may include a proximity sensor, an illuminance sensor, an acceleration sensor, a magnetic sensor, a gyro sensor, an inertial sensor, an RGB sensor, an IR sensor, a fingerprint recognition sensor, an ultrasonic sensor, an optical sensor, a microphone, a Lidar, and a radar.

The output interface 15 may generate an output related to a visual sense, an auditory sense, or a haptic sense.

At this time, the output interface 15 may include a display unit for outputting time information, a speaker for outputting auditory information, and a haptic module for outputting haptic information.

The memory 17 may store data that supports various functions of the AI device 10. For example, the memory 17 may store input data acquired by the input interface 12, learning data, a learning model, a learning history, and the like.

The processor 18 may determine at least one executable operation of the AI device 10 based on information determined or generated by using a data analysis algorithm or a machine learning algorithm. The processor 18 may control the components of the AI device 10 to execute the determined operation.

To this end, the processor 18 may request, search, receive, or utilize data of the learning processor 13 or the memory 17. The processor 18 may control the components of the AI device 10 to execute the predicted operation or the operation determined to be desirable among the at least one executable operation.

If the connection of an external device is required to perform the determined operation, the processor 18 may generate a control signal for controlling the external device and may transmit the generated control signal to the external device.

The processor 18 may acquire intention information for the user input and may determine the user's requirements based on the acquired intention information.

The processor 18 may acquire the intention information corresponding to the user input by using at least one of a speech to text (STT) engine for converting speech input into a text string or a natural language processing (NLP) engine for acquiring intention information of a natural language.

At least one of the STT engine or the NLP engine may be configured as an artificial neural network, at least part of which is learned according to the machine learning algorithm. At least one of the STT engine or the NLP engine may be learned by the learning processor 13, may be learned by the learning processor 24 of the AI server 20, or may be learned by their distributed processing.

The processor 18 may collect history information including the operation contents of the AI apparatus 100 or the user's feedback on the operation and may store the collected history information in the memory 17 or the learning processor 13 or transmit the collected history information to the external device such as the AI server 20. The collected history information may be used to update the learning model.

The processor 18 may control at least part of the components of AI device 10 so as to drive an application program stored in memory 17. Furthermore, the processor 18 may operate two or more of the components included in the AI device 10 in combination so as to drive the application program.

Figure 2:
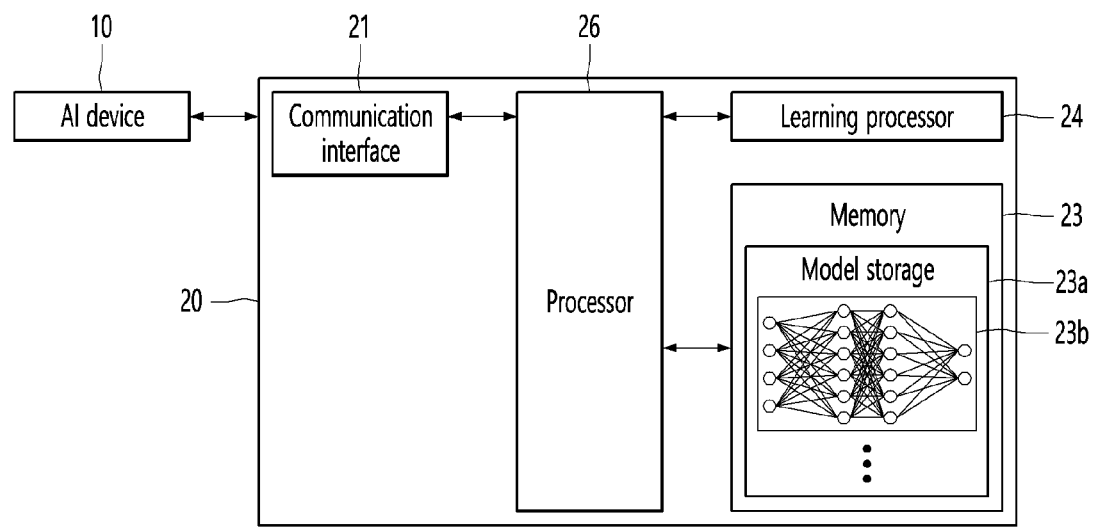
FIG. 2 shows an AI server connected to a robot according to an embodiment of the present invention.

FIG. 2 illustrates an AI server 20 connected to a robot according to an embodiment of the present disclosure.

Referring to FIG. 2, the AI server 20 may refer to a device that learns an artificial neural network by using a machine learning algorithm or uses a learned artificial neural network. The AI server 20 may include a plurality of servers to perform distributed processing, or may be defined as a 5G network. At this time, the AI server 20 may be included as a partial configuration of the AI device 10, and may perform at least part of the AI processing together.

The AI server 20 may include a communication interface 21, a memory 23, a learning processor 24, a processor 26, and the like.

The Communication interface 21 can transmit and receive data to and from an external device such as the AI device 10.

The memory 23 may include a model storage unit 23a. The model storage unit 23a may store a learning or learned model (or an artificial neural network 26b) through the learning processor 24.

The learning processor 24 may learn the artificial neural network 26b by using the learning data. The learning model may be used in a state of being mounted on the AI server 20 of the artificial neural network, or may be used in a state of being mounted on an external device such as the AI device 10.

The learning model may be implemented in hardware, software, or a combination of hardware and software. If all or part of the learning models are implemented in software, one or more instructions that constitute the learning model may be stored in memory 23.

The processor 26 may infer the result value for new input data by using the learning model and may generate a response or a control command based on the inferred result value.

Figure 3:
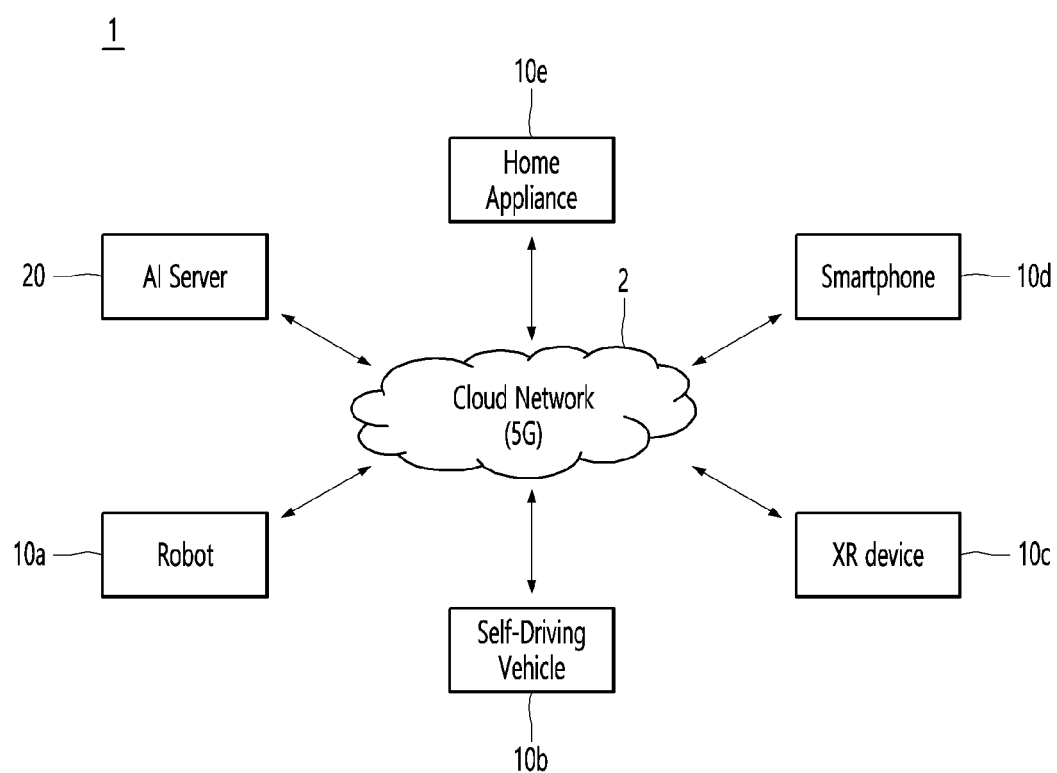
FIG. 3 shows an AI system according to an embodiment of the present invention.

FIG. 3 illustrates an AI system 1 according to an embodiment of the present disclosure.

Referring to FIG. 3, in the AI system 1, at least one of an AI server 20, a robot 10a, a self-driving vehicle 10b, an XR device 10c, a smartphone 10d, or a home appliance 10e is connected to a cloud network 2. The robot 10a, the self-driving vehicle 10b, the XR device 10c, the smartphone 10d, or the home appliance 10e, to which the AI technology is applied, may be referred to as AI devices 10a to 10e.

The cloud network 2 may refer to a network that forms part of a cloud computing infrastructure or exists in a cloud computing infrastructure. The cloud network 2 may be configured by using a 3G network, a 4G or LTE network, or a 5G network.

That is, the devices 10a to 10e and 20 configuring the AI system 1 may be connected to each other through the cloud network 2. In particular, each of the devices 10a to 10e and 20 may communicate with each other through a base station, but may directly communicate with each other without using a base station.

The AI server 20 may include a server that performs AI processing and a server that performs operations on big data.

The AI server 20 may be connected to at least one of the AI devices constituting the AI system 1, that is, the robot 10a, the self-driving vehicle 10b, the XR device 10c, the smartphone 10d, or the home appliance 10e through the cloud network 2, and may assist at least part of AI processing of the connected AI devices 10a to 10e.

At this time, the AI server 20 may learn the artificial neural network according to the machine learning algorithm instead of the AI devices 10a to 10e, and may directly store the learning model or transmit the learning model to the AI devices 10a to 10e.

At this time, the AI server 20 may receive input data from the AI devices 10a to 10e, may infer the result value for the received input data by using the learning model, may generate a response or a control command based on the inferred result value, and may transmit the response or the control command to the AI devices 10a to 10e.

Alternatively, the AI devices 10a to 10e may infer the result value for the input data by directly using the learning model, and may generate the response or the control command based on the inference result.

Hereinafter, various embodiments of the AI devices 10a to 10e to which the above-described technology is applied will be described. The AI devices 10a to 10e illustrated in FIG. 3 may be regarded as a specific embodiment of the AI device 10 illustrated in FIG. 1.

<AI+Robot>

The robot 10a, to which the AI technology is applied, may be implemented as a guide robot, a carrying robot, a cleaning robot, a wearable robot, an entertainment robot, a pet robot, an unmanned flying robot, or the like.

The robot 10a may include a robot control module for controlling the operation, and the robot control module may refer to a software module or a chip implementing the software module by hardware.

The robot 10a may acquire state information about the robot 10a by using sensor information acquired from various kinds of sensors, may detect (recognize) surrounding environment and objects, may generate map data, may determine the route and the travel plan, may determine the response to user interaction, or may determine the operation.

The robot 10a may use the sensor information acquired from at least one sensor among the Lidar, the radar, and the camera so as to determine the travel route and the travel plan.

The robot 10a may perform the above-described operations by using the learning model composed of at least one artificial neural network. For example, the robot 10a may recognize the surrounding environment and the objects by using the learning model, and may determine the operation by using the recognized surrounding information or object information. The learning model may be learned directly from the robot 10a or may be learned from an external device such as the AI server 20.

At this time, the robot 10a may perform the operation by generating the result by directly using the learning model, but the sensor information may be transmitted to the external device such as the AI server 20 and the generated result may be received to perform the operation.

The robot 10a may use at least one of the map data, the object information detected from the sensor information, or the object information acquired from the external apparatus to determine the travel route and the travel plan, and may control the driving unit such that the robot 10a travels along the determined travel route and travel plan.

The map data may include object identification information about various objects arranged in the space in which the robot 10a moves. For example, the map data may include object identification information about fixed objects such as walls and doors and movable objects such as pollen and desks. The object identification information may include a name, a type, a distance, and a position.

In addition, the robot 10a may perform the operation or travel by controlling the driving unit based on the control/interaction of the user. At this time, the robot 10a may acquire the intention information of the interaction due to the user's operation or speech utterance, and may determine the response based on the acquired intention information, and may perform the operation.

<AI+Robot+Self-Driving>

The robot 10a, to which the AI technology and the self-driving technology are applied, may be implemented as a guide robot, a carrying robot, a cleaning robot, a wearable robot, an entertainment robot, a pet robot, an unmanned flying robot, or the like.

The robot 10a, to which the AI technology and the self-driving technology are applied, may refer to the robot itself having the self-driving function or the robot 10a interacting with the self-driving vehicle 10b.

The robot 10a having the self-driving function may collectively refer to a device that moves for itself along the given movement line without the user's control or moves for itself by determining the movement line by itself.

The robot 10a and the self-driving vehicle 10b having the self-driving function may use a common sensing method so as to determine at least one of the travel route or the travel plan. For example, the robot 10a and the self-driving vehicle 10b having the self-driving function may determine at least one of the travel route or the travel plan by using the information sensed through the Lidar, the radar, and the camera.

The robot 10a that interacts with the self-driving vehicle 10b exists separately from the self-driving vehicle 10b and may perform operations interworking with the self-driving function of the self-driving vehicle 10b or interworking with the user who rides on the self-driving vehicle 10b.

At this time, the robot 10a interacting with the self-driving vehicle 10b may control or assist the self-driving function of the self-driving vehicle 10b by acquiring sensor information on behalf of the self-driving vehicle 10b and providing the sensor information to the self-driving vehicle 10b, or by acquiring sensor information, generating environment information or object information, and providing the information to the self-driving vehicle 10b.

Alternatively, the robot 10a interacting with the self-driving vehicle 10b may monitor the user boarding the self-driving vehicle 10b, or may control the function of the self-driving vehicle 10b through the interaction with the user. For example, if it is determined that the driver is in a drowsy state, the robot 10a may activate the self-driving function of the self-driving vehicle 10b or assist the control of the driving unit of the self-driving vehicle 10b. The function of the self-driving vehicle 10b controlled by the robot 10a may include not only the self-driving function but also the function provided by the navigation system or the audio system provided in the self-driving vehicle 10b.

Alternatively, the robot 10a that interacts with the self-driving vehicle 10b may provide information or assist the function to the self-driving vehicle 10b outside the self-driving vehicle 10b. For example, the robot 10a may provide traffic information including signal information and the like, such as a smart signal, to the self-driving vehicle 10b, and automatically connect an electric charger to a charging port by interacting with the self-driving vehicle 10b like an automatic electric charger of an electric vehicle.

Figure 4:
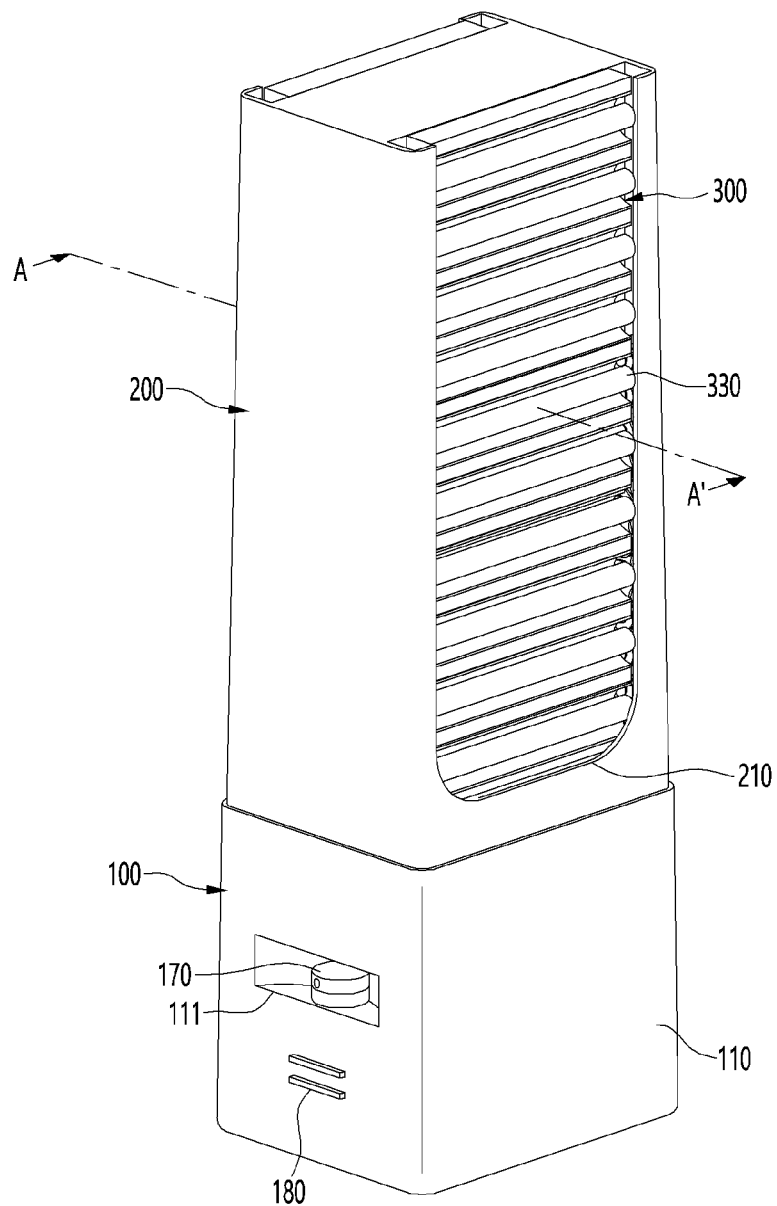
FIG. 4 is a perspective view of a robot according to an embodiment of the present invention.
Figure 5:
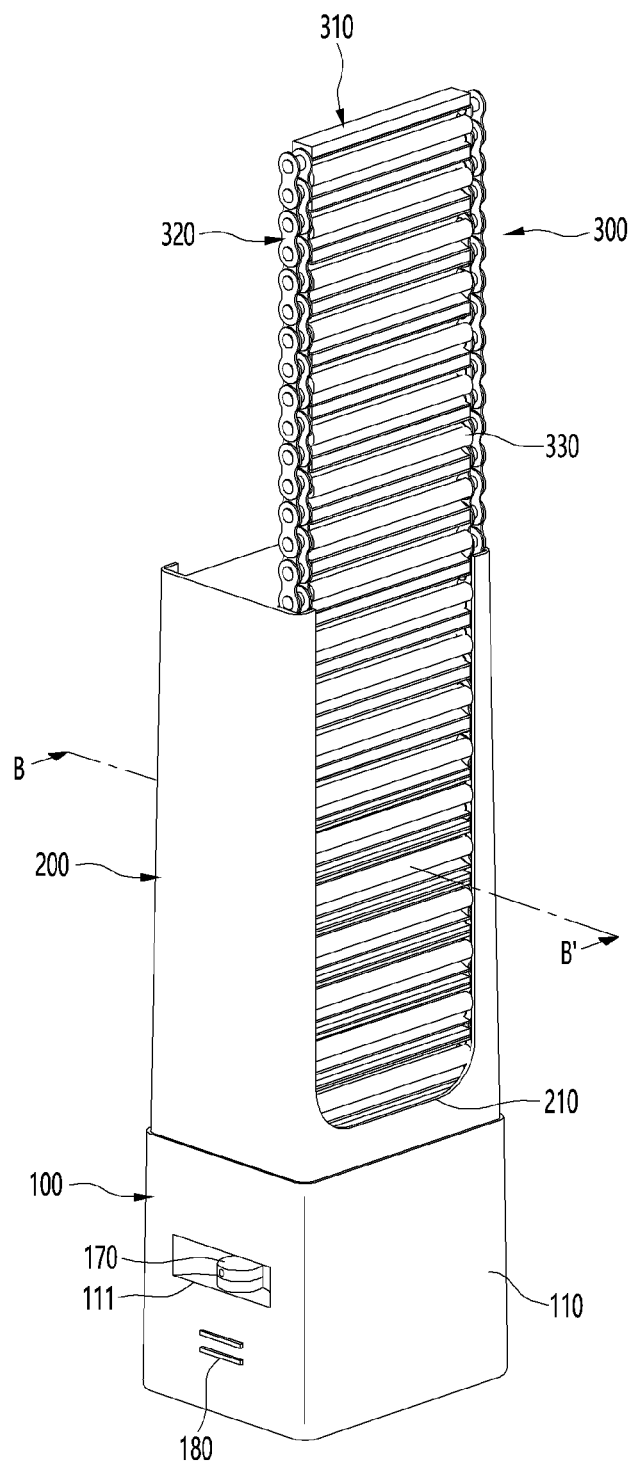
FIG. 5 is a view showing a state in which the sterilization module shown in FIG. 4 is elevated.
Figure 6:
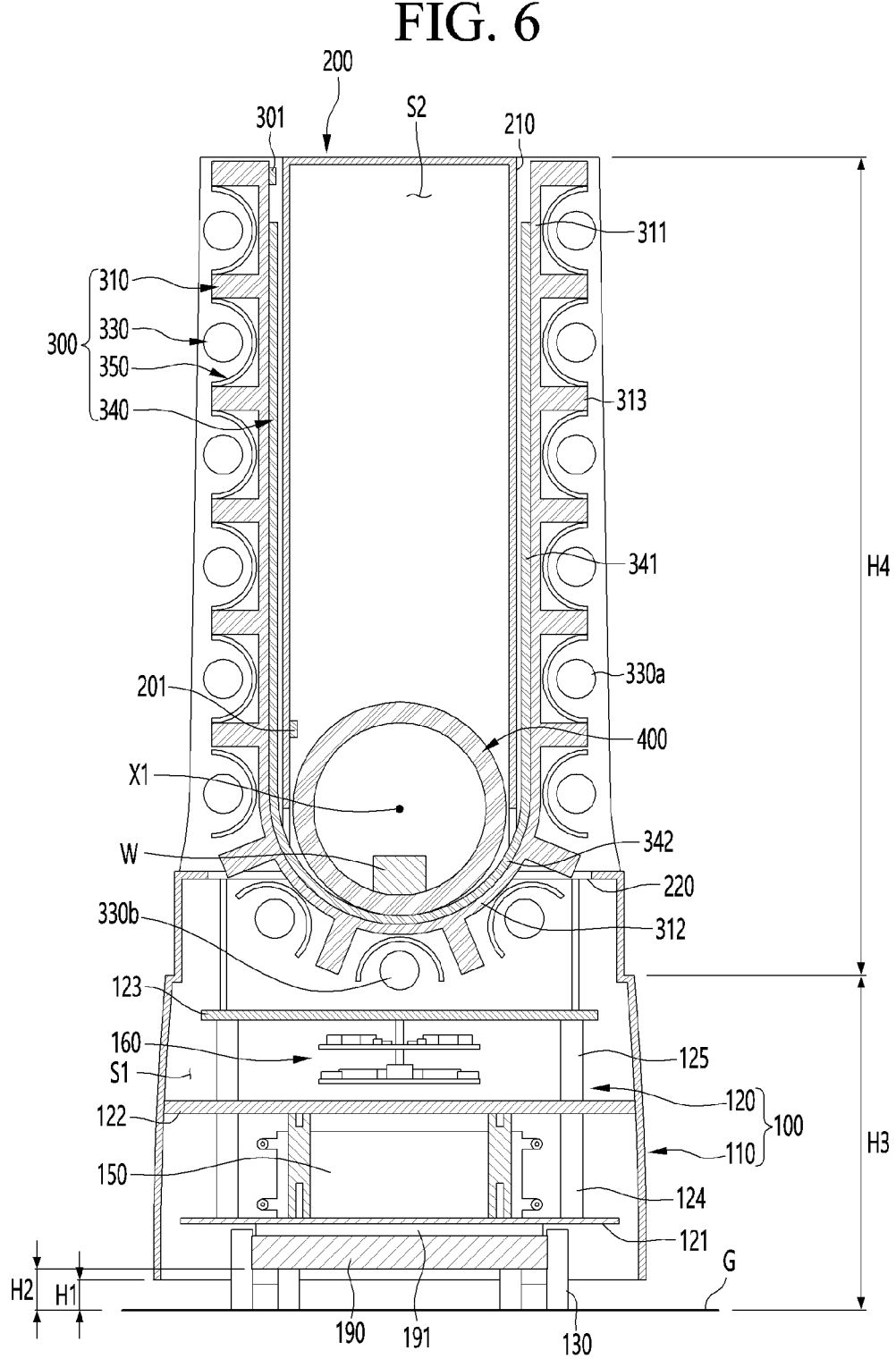
FIG. 6 is a cross-sectional view taken along line A-A' in FIG. 4.
Figure 7:
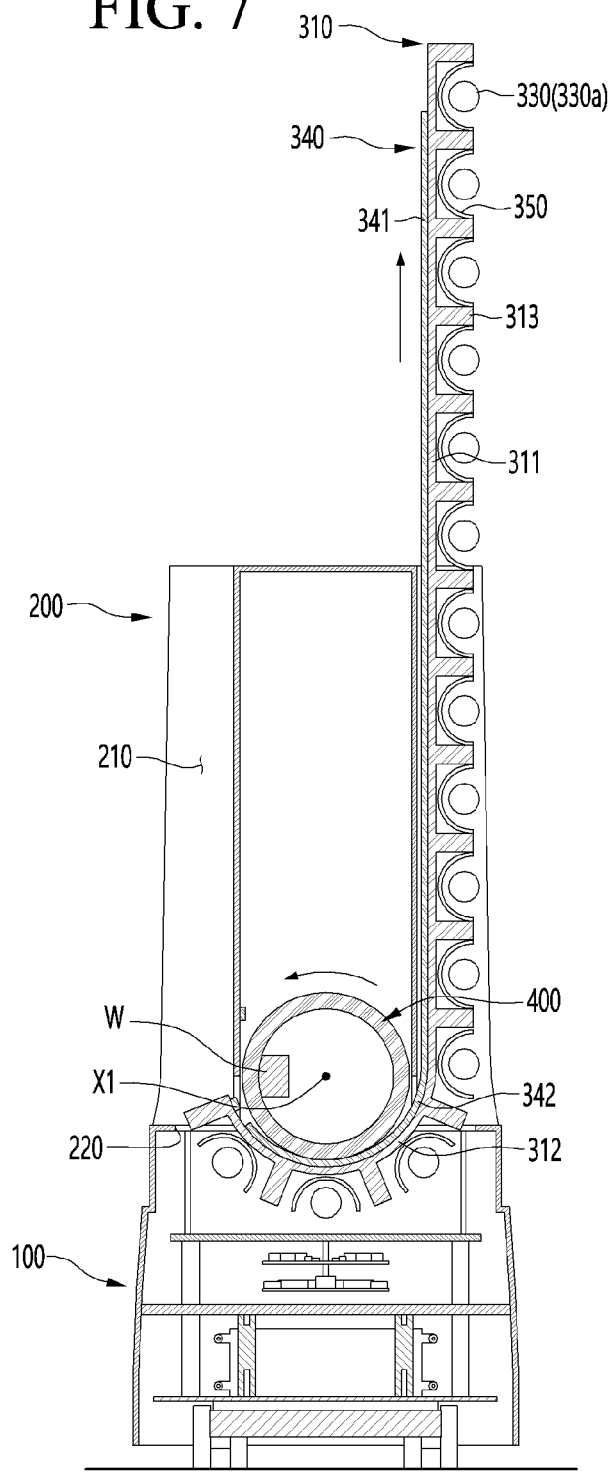
FIG. 7 is a cross-sectional view taken along line BB' of FIG. 5.
Figure 8:
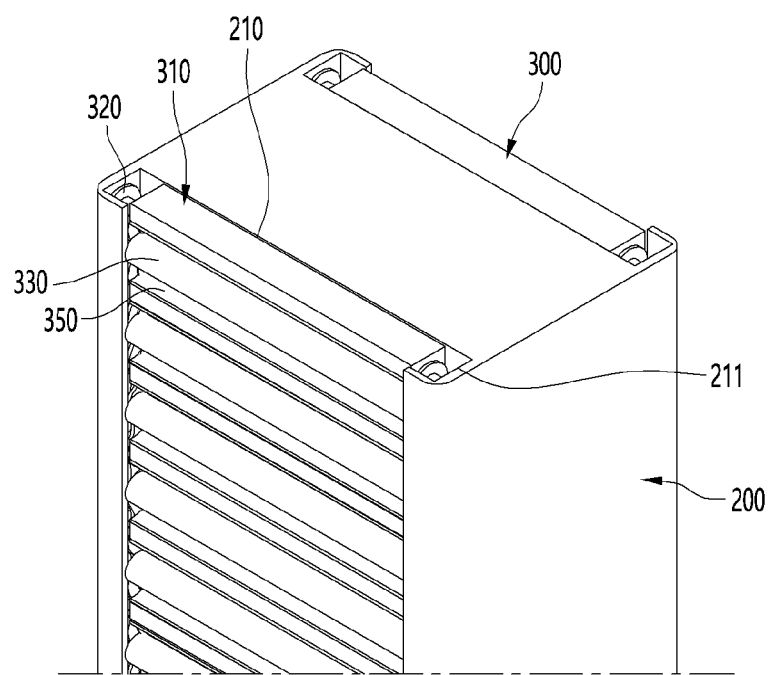
FIG. 8 is an enlarged view of an upper portion of a robot according to an embodiment of the present invention.

FIG. 4 is a perspective view of a robot according to an embodiment of the present invention, FIG. 5 is a view showing a state in which the sterilization module shown in FIG. 4 is elevated, FIG. 6 is a cross-sectional view taken along line A-A' in FIG. 4, FIG. 7 is a cross-sectional view taken along line BB' of FIG. 5, FIG. 8 is an enlarged view of an upper portion of a robot according to an embodiment of the present invention.

A robot according to an embodiment of the present invention may include a base 100, a main body 200 disposed above the base 100, and a sterilization module 300 provided in the main body 200.

The base 100 has an inner space S1 and may constitute the lower part of the robot. A driving wheel 130 may be provided on the base 100. The driving wheel 130 may protrude downward from the base 100 and contact the bottom surface G, thereby enabling the robot to travel.

In more detail, the base 100 may include a case 110 and a base body 120 disposed inside the case 110.

The case 110 may define a circumferential surface of the base 100. The case 110 may surround the base body 120. The case 110 may form an inner space S1 of the base 100.

An opening 111 may be formed on the front surface of the case 110. The Lidar 170 provided on the base 100 may detect an obstacle or the like located in front of the robot through the opening 111. In addition, the base 100 may be provided with a plurality of ultrasonic sensors (not shown) disposed along the circumference of the case 110.

A charging terminal 180 may be provided on the base 100. The charging terminal 180 may protrude from the case 110 in a horizontal direction, for example, forward. A charger (not shown) for charging the robot may be provided on a wall of the room, and the robot may travel toward the charger and contact or connect the charging terminal 180 to the charger.

The base body 120 may include a plurality of plates 121, 122, and 123 and a plurality of support pillars 124 and 125.

The plurality of plates 121, 122, and 123 may be arranged horizontally, and may be parallel to each other and spaced apart in a vertical direction. The plurality of support pillars 124 and 125 may be vertically disposed between the plurality of plates 121, 122 and 123.

Hereinafter, a case in which the plurality of plates 121, 122, and 123 are three will be described as an example. However, the number of the plurality of plates 121, 122, and 123 and the vertical distance between the plates 121, 122, and 123 may vary as needed.

The plurality of plates 121, 122, and 123 may include a base plate 121, a middle plate 122, and a top plate 123. In addition, the plurality of support pillars 124 and 125 include a plurality of lower pillars 124 located between the base plate 121 and the middle plate 122, and a plurality of upper pillars 125 located between the middle plate 122 and the top plate 123.

The base plate 121 may define the lower surface of the base 100.

The driving wheel 130 may be connected to the base plate 121. In addition, casters 140 may be connected to the base plate 121. The number and installation positions of the driving wheels 130 and casters 140 may vary as needed.

For example, a pair of driving wheels 130 may be connected to the front portion of the base 100, and a pair of casters 140 may be connected to the rear portion of the base 100. That is, the robot can travel by front-wheel drive, thereby stably traveling at a low speed.

A battery 150 may be disposed inside the base 100. In more detail, the battery 150 may be disposed between the base plate 121 and the middle plate 122. The battery 150 may supply power required for operation of the robot. The battery 150 may be electrically connected to the charging terminal 180 and may be charged from a charger located outside the robot through the charging terminal 180.

Since the battery 150 is a heavy component, the height of the center of gravity of the robot can be lowered by disposing the battery 150 between the base plate 121 and the middle plate 122. Therefore, there is an advantage that the robot can drive stably.

At least one substrate 160 may be disposed inside the base 100. In more detail, at least one substrate 160 may be disposed between the middle plate 122 and the top plate 123. At least one substrate 160 may include a control board equipped with a processor for controlling overall operation of the robot, an inverter, and a power board electrically connected to a battery. However, it is not limited thereto.

A lower ULTRAVIOLET (Ultra violet) lamp 190 and a lower reflector 191 may be provided on the lower surface of the base 100. In more detail, the lower Ultraviolet lamp 190 and the lower reflector 191 may be positioned below the base plate 121.

The lower Ultraviolet lamp 190 may extend horizontally. For example, the lower Ultraviolet lamp 190 may extend left and right.

The lower Ultraviolet lamp 190 may be suspended and supported on the lower surface of the base 100 by a connecting member (not shown) such as a bracket. The lower Ultraviolet lamps 190 may be spaced downward on the bottom of the base 100. The ultraviolet rays emitted from the lower ultraviolet lamp 190 can sterilize the floor surface G on which the robot travels.

The lower reflector 191 may surround an upper part of the outer circumference of the lower ultraviolet lamp 190 at a distance. The lower reflector 191 may be disposed to pass between the lower surface of the base 100 and the outer circumference of the lower Ultraviolet lamp 190. Accordingly, ultraviolet rays emitted upward from the lower ultraviolet lamp 190 may be reflected downward by the lower reflector 191. As a result, the sterilization efficiency of the bottom surface G of the lower Ultraviolet lamp 190 may be improved.

In addition, the case 110 of the base 100 may cover the lower ULTRAVIOLET lamp 190 in the horizontal direction. That is, the lower ULTRAVIOLET lamp 190 may overlap the lower ULTRAVIOLET lamp 190 in the horizontal direction.

In more detail, the height H2 between the bottom surface G and the lower ULTRAVIOLET lamp 190 may be higher than the height H1 between the bottom surface G and the lower end of the case 110. Therefore, loss of ULTRAVIOLET rays spreading in a horizontal direction from the lower ULTRAVIOLET lamp 190 due to exposure to the outside can be minimized, and a sterilizing effect on the bottom surface G of the lower ULTRAVIOLET lamp 190 can be improved.

Meanwhile, the main body 200 may cover the base 100 from the upper side. The main body 200 may have an inner space S2, and the inner space S2 of the main body 200 may be connected with the inner space S1 of the base 100.

The main body 200 may be integrally formed with the case 110 of the base 100. However, it is not limited thereto, and the main body 200 and the case 100 may be manufactured separately and fastened to each other, of course.

The height H4 of the main body 200 may be formed higher than the height H3 of the base 100.

A pair of depression portions 210 may be formed in the main body 200. A pair of depression portions 210 may be formed on both sides of the main body 200 located opposite to each other. Hereinafter, a case in which a pair of depression portions 210 are formed on both side surfaces of the main body 200 will be described as an example. However, it is not limited thereto, and it is also possible that a pair of depression portions 210 are formed on the front and rear surfaces of the main body 200, of course.

The depression portion 210 may be formed by being depressed inward from the outer circumference of the main body 200. The depression portion 210 may extend substantially vertically.

A part of the sterilization module 300 to be described later may be accommodated in the pair of depression portions 210. Since the depression portion 210 is open horizontally outward, the sterilization module 300 located in the depression portion 210 may radiate ultraviolet rays to the outside of the robot to sterilize indoor walls or structures.

Also, the depression portion 210 may be open to the upper side. Therefore, the sterilization module 300 located in the depression portion 210 may slide upward and protrude upward from the main body 200. Thus, the sterilization module 300 can effectively sterilize up to a position higher than the main body 200 with respect to walls or structures. This will be described in detail later.

In addition, a pair of guide grooves 211 (see FIG. 8) extending vertically and guiding vertical sliding of the sterilization module 300 may be formed on both surfaces facing each other inside each depression portion 210. In more detail, both edges of the sterilization module 300 may be located within the pair of guide grooves 211. Accordingly, it is possible to prevent the sterilization module 300 located in the depression portion 210 from being bent or separated from the depression portion 210. In addition, sliding of the sterilization module 300 in the vertical direction may be guided by the guide groove 211.

A pair of through holes 220 through which the sterilization module 300 passes may be formed in the pair of depression portions 210. Each through hole 220 is formed in the lower portion of the depression portion 210 and may be connected with the inner space S2 of the main body 200.

The sterilization module 300 may have an approximate 'U' shape. The sterilization module 300 may be installed to pass through the pair of through holes 220. Therefore, a part of the sterilization module 300 is located in one of the pair of depression portions 210, another part of the sterilization module 300 is located in the other one of the pair of depression portions 210, and the other part of sterilization module 300 may be located inside the main body 200.

The sterilization module 300 may include a flexible plate 310, a pair of chains 320, a plurality of ultraviolet lamps 330, and a support sheet 340. The sterilization module 300 may further include a plurality of reflectors 350.

The flexible plate 310 has a flexible material and may be integrally formed. For example, the flexible plate 310 may be made of rubber, urethane, or silicon.

The flexible plate 310 may maintain a bent state in a 'U' shape. In more detail, the flexible plate 310 may include a pair of vertical portions 311 and a connection portion 312 connecting the pair of vertical portions 311 to each other.

Each vertical part 311 is located in the depression portion 210 and can slide vertically along the depression portion 210.

The connecting portion 312 may connect lower ends of the pair of vertical portions 311 to each other through a pair of through holes 220 formed in the pair of depression portions 210. The connecting portion 312 may be bent convexly downward. The connecting portion 312 may be bent along the outer circumference of the rotator 400 to be described later. That is, the connecting portion 312 may be bent with respect to the rotation axis X1 of the rotator 400.

At least a portion of the connection portion 312 may be located at a height lower than the through hole 220 in the inner space S2 of the main body 200, more specifically, in the inner space S2 of the main body 200.

The pair of vertical portions 311 and connection portions 312 of the flexible plate 310 are not fixed, and may change according to the sliding of the flexible plate 310.

For example, if the rotator 400 to be described later rotates in one direction, the flexible plate 310 slides, and the height of one vertical portion 311 may increase and the height of another vertical portion 311 may decrease. Conversely, if the rotator 400 to be described later rotates in another direction, the flexible plate 310 slides, and the height of one vertical portion 311 may decrease and the height of the other vertical portion 311 may increase.

In addition, a plurality of ribs 313 may protrude from the flexible plate 310. A plurality of ribs 313 may protrude from the outer surface of the flexible plate 310 and may be spaced parallel to each other.

The plurality of ribs 313 may extend in a horizontal direction, more specifically, in the width direction of the flexible plate 310, and may be spaced apart from each other along the length direction of the flexible plate 310. The plurality of ribs 313 may be spaced apart from each other by a predetermined interval. The plurality of ribs 313 may be spaced apart from each other with an ultraviolet lamp 330 and a reflector 350 interposed therebetween.

The plurality of ribs 313 may support the reflector 350. In addition, the plurality of ribs 313 can prevent the flexible plate 310 from bending only about the rotational axis X1 of the rotator 400 and bending in other directions.

A pair of chains 320 may be coupled to both edges of the flexible plate 310. That is, the pair of chains 320 may be spaced apart from each other in the width direction of the flexible plate 310.

Each chain 320 may extend along the length direction of the flexible plate 310. That is, each chain 320 may also maintain a 'U' shape similarly to the flexible plate 310. In more detail, a part of each chain 320 may correspond to a pair of vertical parts 311 and another part may correspond to a connecting part 312.

A portion corresponding to the pair of vertical portions 311 of each chain 320 may be located within the guide groove 211 formed on both inner surfaces of the depression portion 210.

The pair of chains 320 may be gear-coupled with the rotator 400 to be described later, and transmit rotational force of the rotator 400 to the flexible plate 310. Thus, the flexible plate 310 can slide.

The plurality of ultraviolet lamps 330 may extend in a horizontal direction, more specifically, in a width direction of the flexible plate 310. The plurality of Ultraviolet lamps 330 may be spaced apart from each other along the length direction of the flexible plate 310. The plurality of Ultraviolet lamps 330 may be spaced apart from each other by a predetermined interval.

A plurality of ultraviolet lamps 330 may be disposed on the outer surface of the flexible plate 310. A plurality of ultraviolet lamps 330 may be disposed between the plurality of ribs 313.

The plurality of Ultraviolet lamps 330 may be connected to the flexible plate 310 or the chain 320. In more detail, both ends of each ULTRAVIOLET lamp 330 may be connected to a flexible plate 310 or a chain 320.

The plurality of ultraviolet lamps 330 may include a first ULTRAVIOLET lamp 330a corresponding to the vertical portion 311 and a second ULTRAVIOLET lamp 330b corresponding to the connection portion 312.

A plurality of first ultraviolet lamps 330a may be provided, and may be located inside the depression portion 210 or above the depression portion 210. The plurality of first ultraviolet lamps 330a may be spaced apart from each other in a vertical direction. The robot may move so that the plurality of first ultraviolet ray lamps 330a are adjacent to a sterilization target (example, a wall), and the sterilization target may be sterilized by the plurality of first ultraviolet ray lamps 330a.

At least one second ULTRAVIOLET lamp 330b may be provided and may be located in the inner space S2 of the main body 200. In more detail, the second ULTRAVIOLET lamp 330b may be positioned at a height lower than the through hole 220 in the inner space S2 of the main body 200.

The first ULTRAVIOLET lamp 330a and the second ULTRAVIOLET lamp 330b may be changed according to the sliding of the flexible plate 310. In more detail, one ULTRAVIOLET lamp 330 may become a first ULTRAVIOLET lamp 330a or a second ULTRAVIOLET lamp 330b according to the sliding of the flexible plate 310.

In addition, if one vertical portion 311 rises and the other vertical portion 311 descends according to the sliding of the flexible plate 310, the number of first ultraviolet lamps 330a corresponding to the one vertical portion 311 is increase, and the number of first Ultraviolet lamps 330a corresponding to the other vertical portion 311 may decrease.

The plurality of reflectors 350 may reflect ultraviolet rays emitted toward the inside from the plurality of ultraviolet lamps 330 toward the outside of the main body 200. Accordingly, the sterilization efficiency of the ULTRAVIOLET lamp 330 with respect to the sterilization target (example, wall surface) can be further improved.

A plurality of reflectors 350 may be disposed between the plurality of ribs 313. In more detail, both edges of the reflector 350 may be supported in contact with a pair of ribs 313 adjacent to each other.

The plurality of reflectors 350 may be fixed to the flexible plate 310 by fixing members (not shown) such as pin or screw.

Each reflector 350 may pass between each ULTRAVIOLET lamp 330 and the outer surface of the flexible plate 310. Each reflector 350 may surround a portion of the outer circumference of each ULTRAVIOLET lamp 330 at a distance. That is, the reflector 350 may be bent along the outer circumference of the ULTRAVIOLET lamp 330.

Meanwhile, the support sheet 340 may support the flexible plate 310 from the inside. The support sheet 340 may contact or be adjacent to the inner surface of the flexible plate 310. That is, the support sheet 340 may be positioned on the opposite side of the plurality of ultraviolet lamps 330 with respect to the flexible plate 310.

The support sheet 340 is connected to the flexible plate 310 and can slide together with the flexible plate 310.

The support sheet 340 may have a material having higher rigidity than the flexible plate 310. For example, the support sheet 340 may include a metal or plastic material.

The support sheet 340 is integrally formed and may extend along the longitudinal direction of the flexible plate 310. That is, like the flexible plate 310, the support sheet 340 may also maintain a bent state in a 'U' shape.

In more detail, the support sheet 340 may include a pair of support portions 341 corresponding to the pair of vertical portions 311 and a bending portion 342 corresponding to the connection portion 312.

The support portion 341 may extend vertically. The support portion 341 may support the vertical part 311 of the flexible plate 310 from inside. In particular, as shown in FIG. 7, ig the vertical portion 311 protrudes upward from the main body 200, the support portion 341 may support the one vertical portion 311 so as not to bend inward.

A configuration for preventing the support portion 341 from being bent inward will be described later in detail.

At least a portion of the support portion 341 may be located inside the depression portion 210. In more detail, at least a portion of the support portion 341 may be positioned between the inner surface of the depression portion 210 and the inner surface of the vertical portion 211.

The bending portion 342 may connect the pair of support portions 341 to each other. In more detail, the bending portion 342 may connect lower ends of the pair of support portions 341 to each other through the pair of through holes 220.

The bending portion 342 may be bent convexly downward. The bending portion 342 may be bent along the outer circumference of the rotator 400. That is, the bending portion 342 may be bent with respect to the rotation axis X1 of the rotator 400.

The bending portion 342 may be located between an outer circumference of the rotator 400 and an inner circumference of the connecting portion 312.

The pair of support portions 341 and the bending portion 342 of the support sheet 340 are not fixed and may change according to the sliding of the support sheet 340.

For example, if the rotator 400 to be described later rotates in one direction, the support sheet 340 slides along with the flexible plate 310, and the height of one support portion 341 may increase and the height of the other support portion 341 may decrease. In this case, the portion protruding upward from the main body 200 of the support portion 341 may support the portion of the vertical portion 311 protruding upward from the main body 200 so as not to be bent inward.

Conversely, if the rotator 400, which will be described later, rotates in another direction, the support sheet 340 slides along with the flexible plate 310, and the height of one vertical portion 311 may be increased and the height of the other vertical portion 311 may be decreased. In this case, a portion of the other support portion 341 protruding upward from the main body 200 may be supported so that the portion of the other vertical portion 311 protruding upward from the main body 200 is not bent inward.

Meanwhile, the robot may further include a rotator 400 sliding the sterilization module 300.

The rotator 400 may be located in the inner space S2 of the main body 200. The rotator 400 may be positioned above the bending portion 342 of the support sheet 340. An upper portion of the rotator 400 may be positioned between the pair of depression portions 320.

The rotator 400 may include a pair of gear units 410 (see FIG. 9) gear-coupled with the pair of chains 320 of the sterilization module 300. Thus, the rotational force of the rotator 400 is transmitted to the sterilization module 300, and the sterilization module 300 can slide. The gear unit 410 may be a chain wheel, but is not limited thereto.

The rotator 400 may have a substantially hollow cylindrical shape, but is not limited thereto.

The rotator 400 may rotate in both directions about the horizontal rotation axis X1. The rotation axis X1 may be parallel to the width direction of the sterilization module 300, that is, the extension direction of the ultraviolet lamp 330.

A motor (not shown) for rotating the rotator 400 may be provided in the inner space S2 of the main body 200 or inside the rotator 400.

Meanwhile, the main body 200 may include a weight body W whose position is variable according to the rotation of the rotator 400. The weight body W may be connected to the rotator 400. For example, as shown in FIG. 7, the weight body W is disposed on the inner circumference of the rotator 400 and may be disposed eccentrically with respect to the rotational axis X1 of the rotator 400. However, it is not limited thereto, and it may be possible that the weight body W is provided on a cam (not shown) connected to the rotator 400.

The weight body W may be moved to be closer to one of the pair of vertical portions 311 of the flexible container 310 having a lowered height, or may be eccentric toward the one vertical portion 311. That is, if the vertical part 311 located in one depression portion 210 rises, the weight body W may move adjacent to the other recessed part 210 or be eccentric.

Therefore, the weight body W can minimize the shifting of the center of gravity of the robot to one side by one vertical portion 311 in an elevated state and maintain a weight balance. As a result, the robot can travel stably even if the one vertical part 311 is in an elevated state.

Meanwhile, a sensor 201 for detecting a height of at least one of a pair of vertical portions 311 of the flexible plate 310 may be provided in the robot.

Hereinafter, a case where the sensor 201 is a magnetic sensor that senses a change in a magnetic field generated by a magnet 301 provided in the sterilization module 300 will be described as an example.

The sensor 201 may be provided on the main body 200 or the rotator 400, and the magnet 301 may be disposed at the end of the sterilization module 300 or adjacent to the end of the sterilization module 300. The magnet 301 may be provided on the vertical portion 311 of the flexible plate 310 or the support portion 341 of the support sheet 340.

Therefore, if the rotator 400 rotates and the sterilization module 300 slides, the distance between the sensor 201 and the magnet 301 can be varied. The sensor 201 may detect a change in the magnetic field generated by the magnet 301 and calculate a distance between the sensor 201 and the magnet 301. Thus, the processor 160 of the robot (for convenience, the same code as the 'substrate' is used) can communicate with the sensor 201 to determine the sliding state of the sterilization module 300.

If the detection value of the sensor 201 is within a predetermined range, it means that one vertical portion 311 of the flexible plate 310 does not protrude upward from the main body 200 or is slightly raised upward from the main body 200. can do. Conversely, if the detected value of the sensor 201 is out of the predetermined range, it may mean that one vertical portion 311 of the flexible plate 310 is greatly raised upward than the main body 200.

Accordingly, the processor 160 of the robot may limit the traveling speed of the robot, that is, the rotational speed of the driving wheel 130, if the detected value of the sensor 201 is out of a predetermined range. As a result, in a state where one vertical portion 311 of the flexible plate 310 is greatly raised upward from the body 200, it is possible to stably travel only at a predetermined speed or less.

Figure 9:
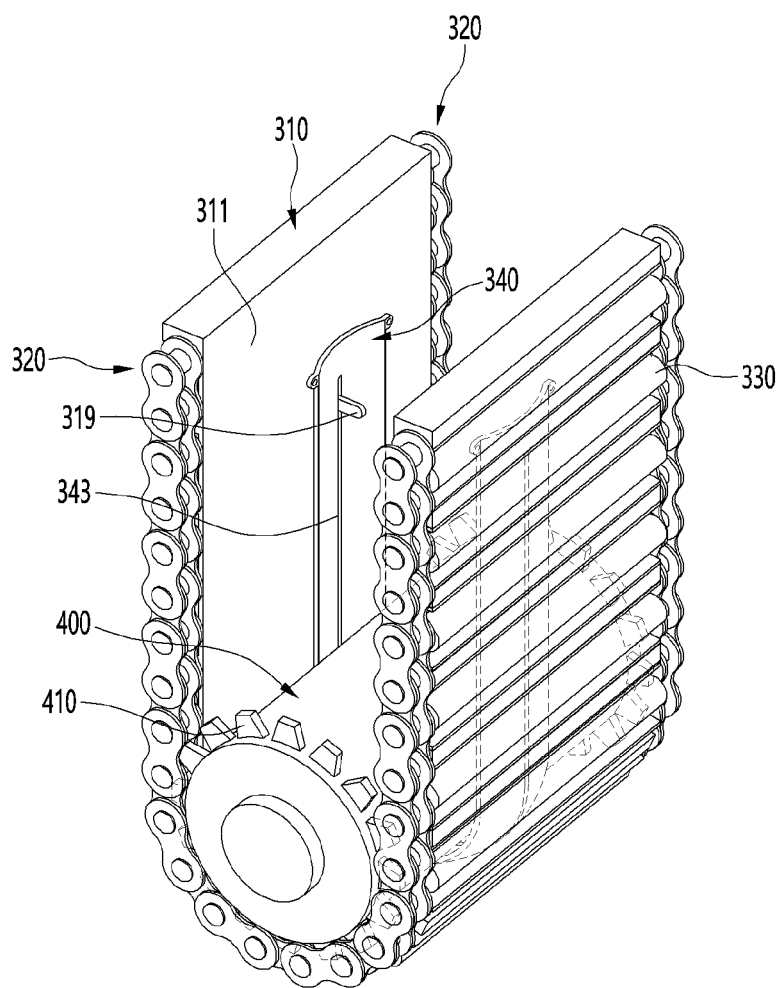
FIGS. 9 and 10 are views for explaining a support sheet according to an embodiment of the present invention.
Figure 10:
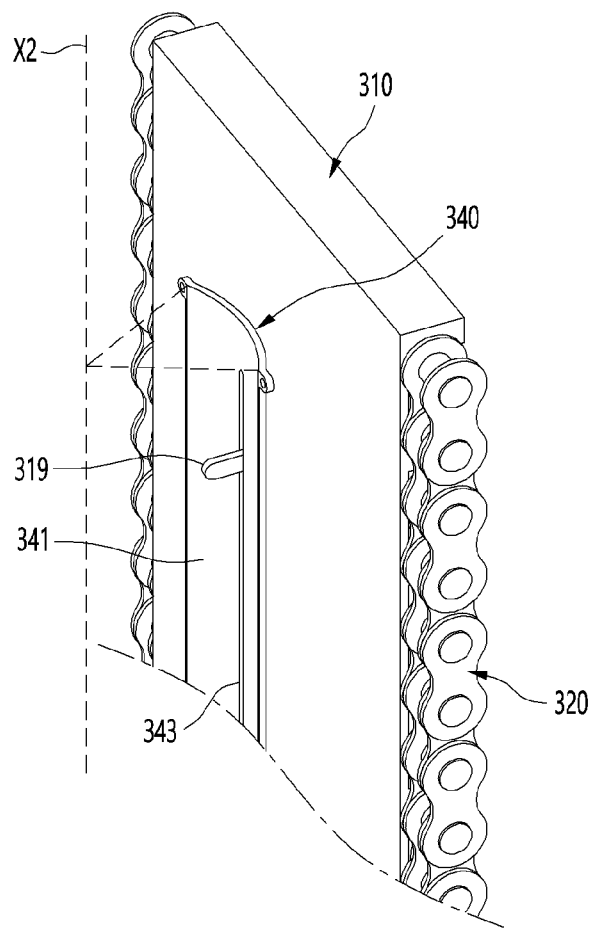

FIGS. 9 and 10 are views for explaining a support sheet according to an embodiment of the present invention.

A guide hole 343 extending in the longitudinal direction of the support sheet 340 may be formed through the support sheet 340. In more detail, the guide hole 343 may be composed of a single hole extending from one support portion 341 to the other support portion 341. Alternatively, the guide holes 343 may be formed in a pair of support portions 341 and provided as a pair separated from each other.

A pair of guide pins 319 protruding from the flexible plate 310 may be inserted into the guide hole 343. The pair of guide pins 319 may protrude inward from the pair of vertical portions 311 of the flexible plate 310. The guide pin 319 may slide with respect to the guide hole 343.

The support sheet 340 may slide along with the flexible plate 310 by the guide pin 319 and the guide hole 343. Also, the support sheet 340 may be constrained with respect to the width direction of the flexible plate 310.

If one vertical portion 311 of the flexible plate 310 rises and the other vertical portion 311 descends, the guide pin 319 protruding from the one vertical portion 311 can be raised together with the one vertical portion 311 to be caught on one end of the guide hole 343, and one support portion 341 of the support sheet 340 can be pulled upward. Therefore, one support portion 341 of the support sheet 340 may rise together with the one vertical part 311, and the other support portion 341 may descend.

Meanwhile, the pair of support portions 341 of the support sheet 340 may be convexly bent toward the inner surface of the flexible plate 310 with respect to the vertical axis X2. In more detail, each support portion 341 may be convexly bent toward the inner surface of the vertical part 311 of the flexible plate 310 with respect to the vertical axis X2.

Also, the bending portion 342 (see FIG. 6) of the support sheet 340 may be bent with respect to the horizontal axis X1 of the rotator 400. That is, the support portion 341 and the bending part 342 may be bent with respect to axes in different directions.

In more detail, the support sheet 340 may be a bistable (Bi-stable) member. A representative example of such a bistable member is a metal tapeline.

If the support sheet 340 is not provided in the sterilization module 300 and exists alone, the support sheet 340 has a first stable state which is bent with respect to a bending axis parallel to the longitudinal direction, and a second stable state which is parallel to a straight line in the longitudinal direction of the support sheet 340.

On the other hand, if the support sheet 340 is provided in the sterilization module 300, the bending portion 342 is unfolded with respect to the bending axis and bent with respect to the horizontal axis X1. Accordingly, a restoring force to return to the first and second stable states is generated in the bending portion 342.

The restoring force acts in a direction in which the pair of support portions 341 move away from each other. That is, the pair of support portions 341 may push the pair of vertical parts 311 of the flexible plate 310 outward. Thus, the support portion 341 may support the vertical portion 311 of the flexible plate 310 from the inside.

Figure 11A:
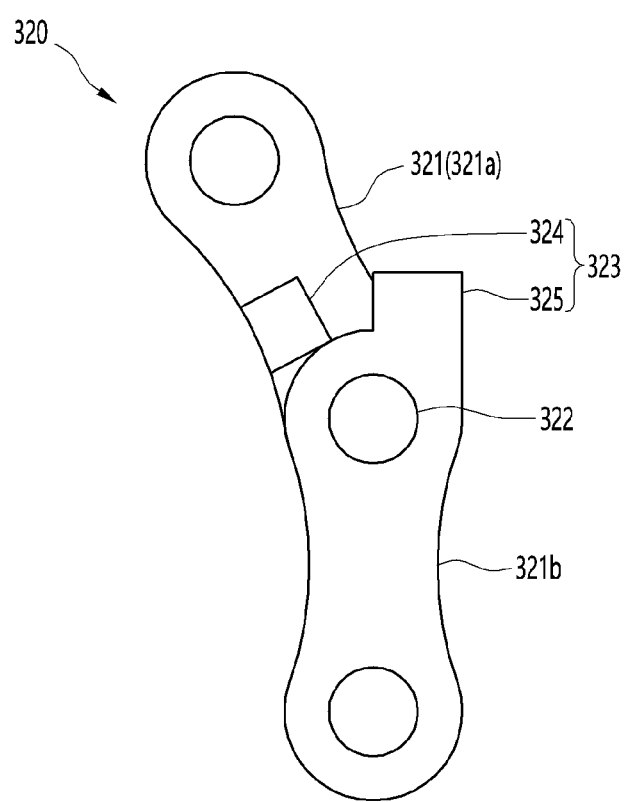
FIGS. 11A and 11B are diagrams illustrating a stopper of a chain according to an embodiment of the present invention.
Figure 11B:
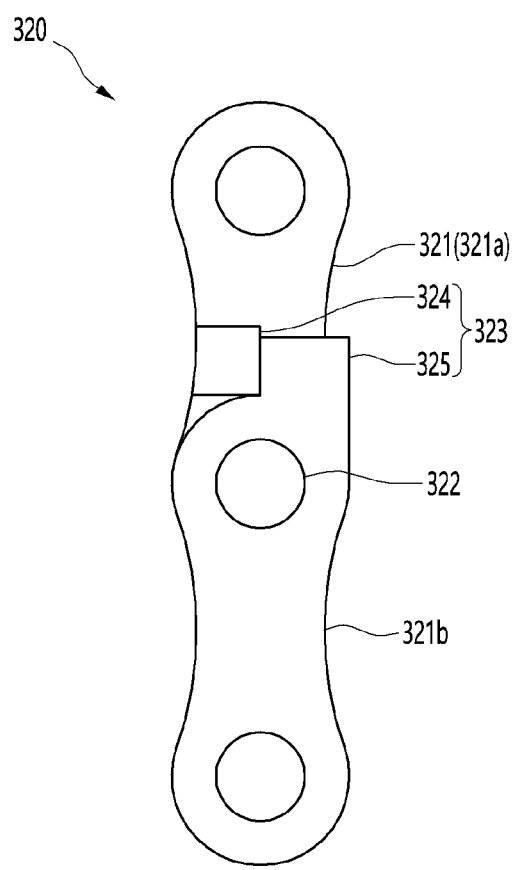

FIGS. 11A and 11B are diagrams illustrating a stopper of a chain according to an embodiment of the present invention.

The chain 320 may include a plurality of plates 321 connected by pins 322. Since the configuration of the chain 320 is a well-known technology, a detailed description thereof will be omitted.

The chain 320 may be provided with a stopper 323 preventing the chain 320 from being bent outward. A plurality of stoppers 323 may be provided.

In more detail, each stopper 323 includes a first protrusion 324 provided on one plate 321a and a second protrusion 325 provided on another plate 321b connected to the one plate 321a by a pin 322.

The one plate 321a may be located closer to the end of the chain 320 than the other plate 321b. That is, if the one plate 321a and the other plate 321b are positioned to correspond to the vertical portion 311 of the flexible plate 310, the one plate 321a may be positioned higher than the other plate 321b.

In this case, the first protrusion 324 may be located inside the second protrusion 325. Accordingly, the one plate 321a may rotate outwardly about the pin 322 with respect to the other plate 321b until the first protrusion 324 comes into contact with the second protrusion 325.

That is, the first protrusion 324 and the second protrusion 325 may selectively contact each other. In more detail, if the one plate 321*a* and the other plate 321*b* are aligned, the first protrusion 324 and the second protrusion 325 may contact each other.

Accordingly, the stopper 323 resists the restoring force of the support sheet 340 and prevents the chain 320 and the vertical portion 311 of the flexible plate 310 connected thereto from being bent outward. As a result, the chain 320 and the flexible plate 310 connected thereto may be maintained in a vertical state.

In addition, by the stopper 323, the chain 320 does not bend outwardly, but it is possible to bend inwardly. Accordingly, the chain 320 can be bent along the connecting portion 312 (see FIG. 6) of the flexible plate 310.

Figure 12:
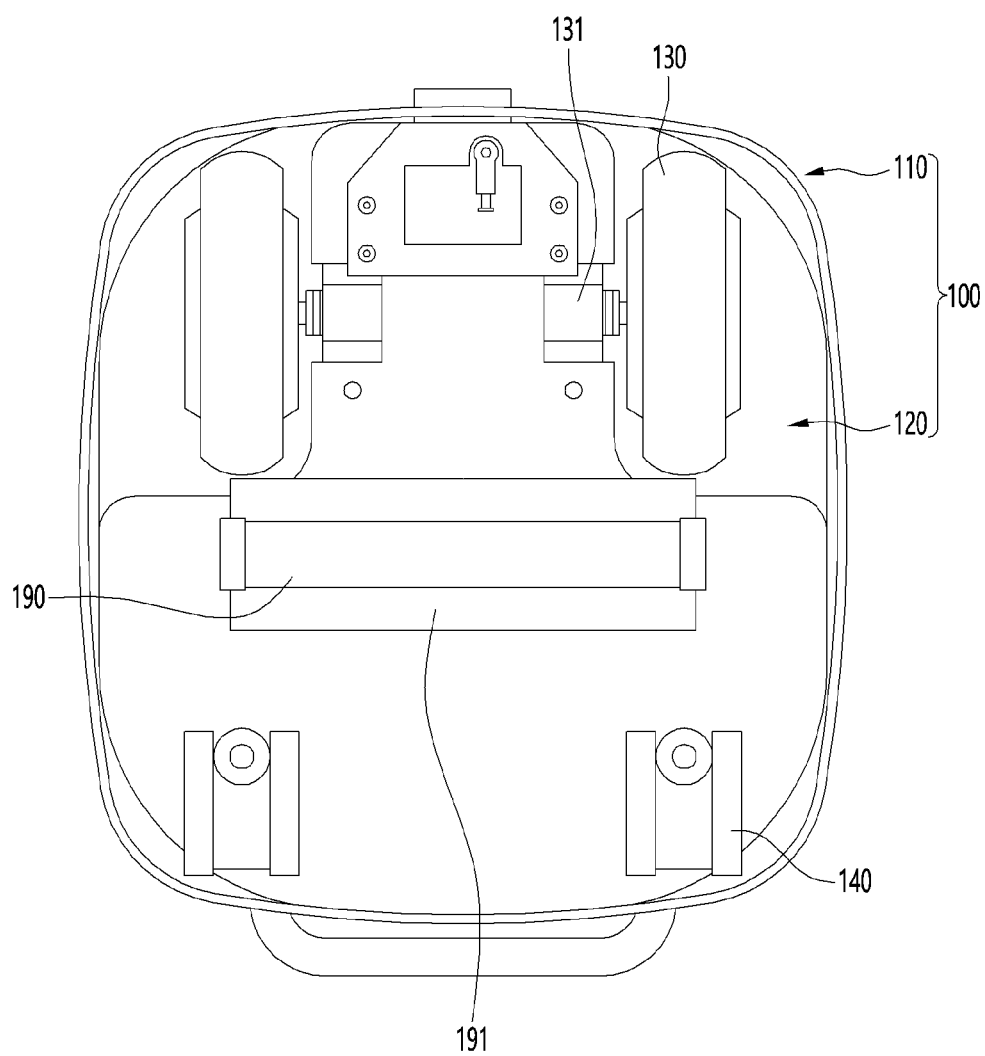
FIG. 12 is a bottom view of a robot according to an embodiment of the present invention.
Figure 13:
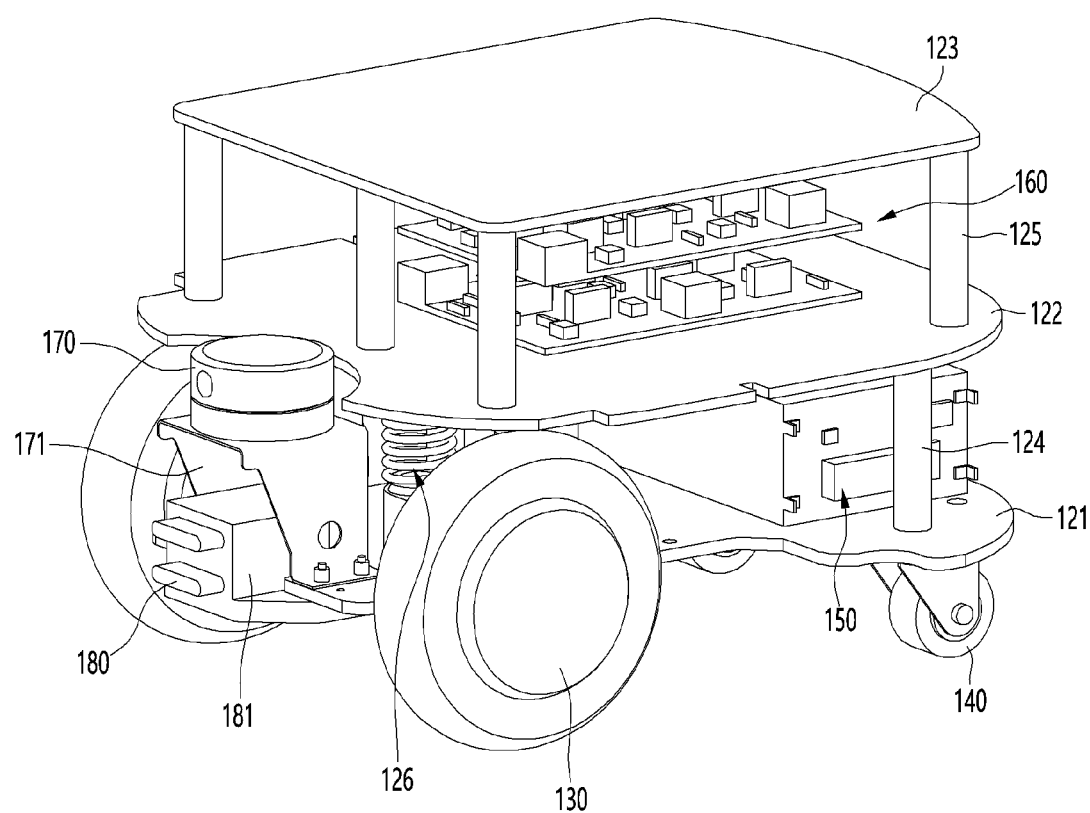
FIG. 13 is a perspective view of a base body according to an embodiment of the present invention.
Figure 14:
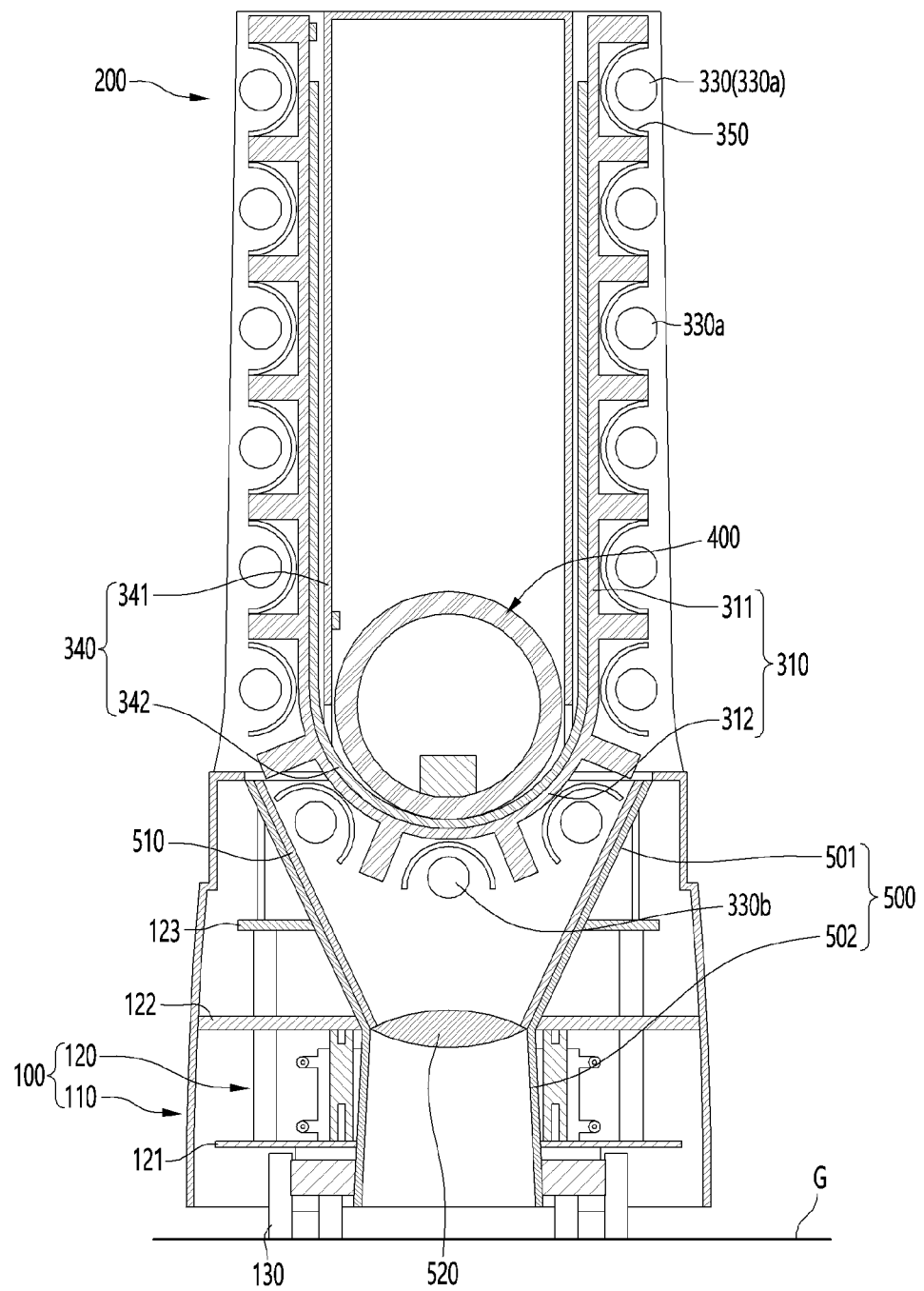
FIG. 14 is a cross-sectional view showing the inside of a robot according to another embodiment of the present invention.

FIG. 12 is a bottom view of a robot according to an embodiment of the present invention, and FIG. 13 is a perspective view of a base body according to an embodiment of the present invention.

A driving motor 131 for rotating the driving wheel 130 may be provided in the base body 120. In more detail, the travel motor 131 may be coupled to the base plate 121 and the travel wheel 130 may be connected to the travel motor 131. However, it is not limited thereto, and the driving wheel 130 may be an in-wheel motor with a built-in motor.

In addition, the base body 120 may be provided with a suspension 126 connected to the driving wheel 130. A pair of suspensions 126 corresponding to the pair of driving wheels 130 may be provided.

In more detail, the suspension 126 may be positioned between the base plate 121 and the middle plate 122. The suspension 126 includes a shaft extending vertically between the base plate 121 and the middle plate 122, and a spring damper disposed on the outer circumference of the shaft and absorbing shock transmitted to the driving wheel 130.

In addition, the Lidar 170 and the charging terminal 180 may be mounted on the base body 120. Lidar 170 and the charging terminal 180 may be located in front of the battery 150.

In more detail, the Lidar mounter 171 equipped with the Lidar 170 and the charging unit 181 equipped with the charging terminal 180 may be fastened to the base plate 121. Lidar 170 may be located on the upper side of the charging unit 181. The Lidar mounter 171 and the charging unit 181 may be fastened to the front portion of the base plate 121.

Meanwhile, the lower ULTRAVIOLET lamp 190 may be disposed between the driving wheel 130 and the caster 140. In more detail, the lower ULTRAVIOLET lamp 190 may extend left and right. A pair of driving wheels 130 may be positioned in front of the lower ULTRAVIOLET lamp 190, and at least one caster 140 may be positioned behind the lower ULTRAVIOLET lamp 190.

Therefore, the driving wheel 130, the lower ULTRAVIOLET lamp 190, and the caster 140 can be efficiently disposed on the base 100 having a limited size.

14 is a cross-sectional view showing the inside of a robot according to another embodiment of the present invention.

The robot according to the present embodiment is the same as the previous embodiment except for the light guide passage 500 and components related thereto. Therefore, overlapping contents are omitted and the description is focused on the differences.

The robot according to the present embodiment may include a light guide passage 500 for guiding ultraviolet light emitted from the ultraviolet lamp 330 of the sterilization module 300 to the bottom surface G contacted by the driving wheel 130. That is, the light guide passage 500 can sterilize the bottom surface G instead of the lower ULTRAVIOLET lamp 190 (see FIG. 12) and the lower reflector 191 described above.

The light guide passage 500 may be located inside the base 100. An upper end of the light guide passage 500 may be positioned above the top plate 123 and a lower end of the light guide passage 500 may be positioned below the base plate 121. That is, open portion through which the light guide passage 500 passes may be formed in the plurality of plates 121, 122, and 123 of the base 100.

The light guide passage 500 may be located below the sterilization module 300, more specifically, the connecting portion 312 of the flexible plate 310 and the corresponding second ULTRAVIOLET lamp 330*b*.

Accordingly, the second ULTRAVIOLET lamp 330*b* may face the inside of the light guide passage 500. The light guide passage 500 may guide ultraviolet light emitted from the second ultraviolet light lamp 330*b* to the bottom surface G.

A mirror 510 may be provided on an inner circumference of the light guide passage 500. Accordingly, the ultraviolet rays emitted into the light guide passage 500 from the second ultraviolet lamp 330*b* may be irradiated to the bottom surface G without loss of output.

In addition, a convex lens 520 may be provided inside the light guide passage 500. Accordingly, ultraviolet light emitted from the second ultraviolet light lamp 330*b* into inner of light guide passage 500 may pass through the convex lens 520 and be refracted. Therefore, since the ultraviolet light passing through the convex lens 520 converges toward the bottom surface G, the sterilizing effect of the bottom surface G may be greater.

In more detail, the light guide passage 500 may include an upper passage 501 positioned above the convex lens 520 and a lower passage 502 positioned below the convex lens 520. That is, the convex lens 520 may form a boundary between the upper passage 501 and the lower passage 502.

The inner cross-sectional area of the upper passage 501 may decrease toward the lower side. For example, the upper passage 501 may have a tapered shape. Also, the mirror 510 may be disposed on an inner circumference of the upper passage 501. Therefore, the ultraviolet rays emitted from the second ultraviolet lamp 330*b* can be smoothly gathered to the convex lens 520 by the shape of the upper passage 501 and the mirror 510, and irradiated to the bottom surface G without loss of output.

Thus, it is possible to sterilize even the bottom surface G with only the plurality of ultraviolet lamps 330 included in the sterilization module 300 without a separate lower ultraviolet lamp 190 (see FIG. 12).

The above description is merely an example of the technical idea of the present invention, and various modifications and variations can be made to those skilled in the art without departing from the essential characteristics of the present invention.

Therefore, the embodiments disclosed in the present invention are not intended to limit the technical idea of the present invention, but to explain, and the scope of the technical idea of the present invention is not limited by these embodiments.

The protection scope of the present invention should be construed according to the following claims, and all technical ideas within the equivalent range should be construed as being included in the scope of the present invention.

The invention claimed is:

1. A robot comprising:
a base comprising a driving wheel;
a main body disposed above the base and comprising an inner space;
a pair of depression portions extending vertically on opposite sides of the main body to be open at an upper side of the main body, wherein the main body comprises openings at a lower end providing access between the depression portions and the inner space of the main body;
a sterilization module comprising:
a flexible plate configured to slide along the pair of depression portions and passing through the openings;
a chain coupled to the flexible plate and extending along a length of the flexible plate; and
a plurality of ultraviolet lamps coupled to the flexible plate or chain and spaced apart from each other; and
a rotator including a gear unit engaged with the chain and disposed in the inner space of the main body, wherein the sterilization module is moved in response to rotation of the rotator,
wherein based on the flexible plate being in a centered position with respect to the rotator, the flexible plate comprises a pair of vertical portions and a connecting portion between the vertical portions and curved around the rotator.

2. The robot of claim 1, wherein the rotator is configured to, rotate to extend one side of the flexible plate out of and above the main body.

3. The robot of claim 2, further comprising a weight body coupled to the rotator and having a variable position according to rotation of the rotator, wherein the weight body is configured to be moved toward a side corresponding to a lower positioned vertical portion among the pair of vertical portions.

4. The robot of claim 1, further comprising guide grooves extending vertically and configured to guide vertical sliding of the chain at opposing inner surfaces of the depression portion.

5. The robot of claim 1, wherein the flexible plate comprises a plurality of protruding ribs respectively separating each of the plurality of ultraviolet lamps.

6. The robot of claim 5, further comprising a plurality of reflectors respectively disposed between each of the plurality of ultraviolet lamps and the flexible plate.

7. The robot of claim 6, wherein each reflector is curved around an inwardly facing side of a circumference of a corresponding ultraviolet lamp.

8. The robot of claim 1, further comprising a support sheet configured to support the flexible plate and comprising a pair of support portions for supporting the vertical portions.

9. The robot of claim 8, wherein each of the pair of support portions are convexly curved toward a respective inner surface of the flexible plate along a vertical axis.

10. The robot of claim 8, wherein the support sheet is disposed between the outer circumference of the rotator and the inner surface of the connection portion.

11. The robot of claim 8, wherein:
the support sheet comprises a guide hole extending in a longitudinal direction of the support sheet; and
a guide pin protrudes from the flexible plate and through the guide hole of the support sheet.

12. The robot of claim 1, wherein the chain comprises a plurality of stoppers configured to prevent the chain from bending outward.

13. The robot of claim 1, further comprising a lower ultraviolet lamp disposed at a lower side of the base.

14. The robot of claim 13, further comprising a lower reflector configured to downwardly reflect ultraviolet light emitted by the lower ultraviolet lamp.

15. The robot of claim 13, wherein the base further comprises:
a base plate on which the lower ultraviolet lamp is disposed; and
a case surrounding the circumference of the base plate,
wherein a height between a bottom surface contacted by the driving wheel and the lower ultraviolet lamp is greater than a height between the bottom surface and a lower end of the case.

16. The robot of claim 1, wherein:
a first ultraviolet lamp of the plurality of ultraviolet lamps-corresponding is positioned at one of the pair of vertical portions positioned at a respective depression portion or above the main body; and
a second ultraviolet lamp of the plurality of ultraviolet lamps is positioned at the connecting portion and located in the inner space of the main body.

17. The robot of claim 16, further comprising:
a light guide path disposed inside the base and configured to guide ultraviolet rays emitted from the second ultraviolet lamp toward a bottom surface in contact with the driving wheel.

18. The robot of claim 17, further comprising:
a mirror provided on an inner surface of the light guide passage; or
at least one of convex lenses disposed inside the light guide passage.

19. The robot of claim 1, further comprising:
a sensor configured to detect a height of at least one of the pair of vertical portions; and
a processor configured to limit a rotational speed of the driving wheel based on the detected height being out of a predetermined range.

* * * * *